US009574190B2

(12) United States Patent
Suga et al.

(10) Patent No.: US 9,574,190 B2
(45) Date of Patent: Feb. 21, 2017

(54) SCREENING METHOD FOR PEPTIDE BINDING TO TARGET MOLECULE IN PH-DEPENDENT MANNER

(71) Applicant: The University of Tokyo, Tokyo (JP)

(72) Inventors: Hiroaki Suga, Tokyo (JP); Takeo Iida, Tokyo (JP)

(73) Assignee: The University of Tokyo, Tokyo (JP)

(*) Notice: Subject to any disclaimer, the term of this patent is extended or adjusted under 35 U.S.C. 154(b) by 0 days.

(21) Appl. No.: 14/405,108

(22) PCT Filed: Jun. 6, 2013

(86) PCT No.: PCT/JP2013/065689
§ 371 (c)(1),
(2) Date: Dec. 2, 2014

(87) PCT Pub. No.: WO2013/183707
PCT Pub. Date: Dec. 12, 2013

(65) Prior Publication Data
US 2015/0133630 A1    May 14, 2015

(30) Foreign Application Priority Data
Jun. 6, 2012   (JP) .................................. 2012-129056

(51) Int. Cl.
| | |
|---|---|
| C12N 15/10 | (2006.01) |
| C07K 7/08 | (2006.01) |
| G01N 33/574 | (2006.01) |
| A61K 47/48 | (2006.01) |
| C07K 7/64 | (2006.01) |
| G01N 33/68 | (2006.01) |
| C07K 7/06 | (2006.01) |

(52) U.S. Cl.
CPC ..... *C12N 15/1068* (2013.01); *A61K 47/48246* (2013.01); *C07K 7/06* (2013.01); *C07K 7/08* (2013.01); *C07K 7/64* (2013.01); *C12N 15/1041* (2013.01); *G01N 33/57492* (2013.01); *G01N 33/6845* (2013.01); *G01N 2500/04* (2013.01)

(58) Field of Classification Search
None
See application file for complete search history.

(56) References Cited

U.S. PATENT DOCUMENTS

| | | |
|---|---|---|
| 2011/0195483 A1 | 8/2011 | Tian et al. |
| 2012/0003210 A1 | 1/2012 | Farrington et al. |
| 2013/0336963 A1 | 12/2013 | Igawa et al. |
| 2015/0315241 A1 | 11/2015 | Hoffmann et al. |

FOREIGN PATENT DOCUMENTS

| | | |
|---|---|---|
| CA | 2431858 A1 | 6/2003 |
| JP | 2005-529837 | 10/2005 |
| JP | 2010-534066 A | 11/2010 |
| JP | 2011-172587 | 9/2011 |
| JP | 2012-021004 | 2/2012 |
| JP | 2012-503991 A | 2/2012 |
| WO | 2003105757 A1 | 12/2003 |
| WO | 2005047327 A1 | 5/2005 |
| WO | 2011044563 A2 | 4/2011 |
| WO | 2012033953 A1 | 3/2012 |

OTHER PUBLICATIONS

Igawa et al., Nature Biotechnology (2020) 28, 1203-1207.*
Odegrip et al., PNAS (2004) 101(9), 2806-2810).*
De Filippis et al., Protein Science (2006) 15, 976-986.*
Millward et al., ACA Chem Biol. (2007) 2(9), 625-634.*
Mezo et al., PNAS (2008) 105(7), 2337-2342).*
Extended European Search Report received in EP 13801033. 5 , mailed Feb. 8, 2016.
Horne, et al., "Antiviral Cyclic D, L-a-Peptides: Targeting a General Biochemical Pathway in Virus Infections", Sep. 1, 2015, pp. 5145-5153, vol. 13, No. 17, Publisher: Bioorganic & Medicinal Chemistry.
Igawa, et al., "Antibody recycling by engineered pH-dependent antigen binding improves the duration of antigen neutralization", Nov. 1, 2010, pp. 1203-1207, vol. 28, No. 11, Publisher: Nature Biotechnology.
Mezo, et al., "X-ray Crystal Structures of Monomeric and Dimeric Peptide Inhibitors in Complex with the Human Neonatal Fc Receptor, FcRn", Sep. 3, 2010, pp. 27694-27701, vol. 285, No. 36, Publisher: J Biol Chem.
Mezo, et al., "PEGylation enhances the therapeutic potential of peptide antagonists of the neonatal Fc receptor, FcRn", Aug. 31, 2011, pp. 6332-6335, vol. 21, No. 21, Publisher: Bioorganic & Medicinal Chemistry Letters.
Mezo, et al., "Structure-activity relationships of a peptide inhibitor of the human FcRn:human IgG interaction", Jun. 15, 2008, pp. 6394-6405, vol. 16, No. 12, Publisher: Bioorganic & Medicinal Chemistry, Pergamon, GB.
Mezo, et al., "Reduction of IgG in nonhuman primates by a peptide antagonist of the neonatal Fc receptor FcRn", Feb. 19, 2008, pp. 2337-2342, vol. 105, No. 7, Publisher: PNAS.
Qiao, et al., "Dependence of antibody-mediated presentation of antigen on FcRn", Jul. 8, 2008, pp. 9337-9342, vol. 105, No. 27, Publisher: PNAS.
Sockolosky, et al., "Engineering neonatal Fc receptor-mediated recycling and transcytosis in recombinant proteins by short terminal peptide extensions", Oct. 2, 2012, pp. 16095-16100, vol. 109, No. 40, Publisher: PNAS.
Vincent, et al., "Current strategies in antibody engineering: Fc engineering and pH-dependent antigen binding, bispecific antibodies and antibody drug conjugates", Dec. 1, 2012, pp. 1444-1450, vol. 7, No. 12, Publisher: Biotechnology Journal.
White, et al., "Contemporary strategies for peptide macrocyclization", Jul. 1, 2011, pp. 509-524, vol. 3, No. 7, Publisher: Nature Chemistry.

* cited by examiner

Primary Examiner — Marcela M Cordero Garcia
Assistant Examiner — Catherine Mader
(74) Attorney, Agent, or Firm — Suzannah K. Sundby, Esq.; Canady + Lortz LLP

(57) ABSTRACT

An object of the present invention is to provide molecules that bind to a target molecule in a pH dependent manner and a screening method for selecting such molecules. Provided is a screening method for selecting peptides that bind to a target molecule at a first pH and do not bind thereto at a second pH, including a step of preparing a peptide library in which each peptide contains at least one special amino acid that undergoes a pH-dependent change in the charge of the side chain thereof, a step of bringing the peptide library into contact with the target molecule and incubating them under the first pH condition and selecting peptides that bind to the target molecule, and a step of selecting, from the peptides which have bound to the target molecule, peptides that do not bind to the target molecule under the second pH condition.

23 Claims, 4 Drawing Sheets

US 9,574,190 B2

SCREENING METHOD FOR PEPTIDE BINDING TO TARGET MOLECULE IN PH-DEPENDENT MANNER

TECHNICAL FIELD

The present invention relates to a screening method for selecting molecules that bind to a target molecule at a certain pH and do not bind to the target molecule at another pH.

BACKGROUND ART

A neonatal Fc receptor (FcRn) has been found as a receptor having a function of transporting an antibody from the fetus to the mother through the placenta. It has recently been suggested that in adults, it contributes to homeostasis of the blood level of an antibody. Both of these functions are caused by pH-dependent binding between IgG and FcRn. This pH dependence is remarkably drastic. Although they bind to each other with a dissociation constant of several nm at pH 6, they hardly bind to each other at pH 7.4. A protein or peptide in the blood has a short half-life because it is brought into an endosome by pinocytosis and is degraded in a lysosome (FIG. 5A). Due to a pH change to acidic in an endosome, an antibody can bind to FcRn that has been expressed in the endosome. The antibody that has bound to FcRn can use an exocytosis pathway so that it is eventually presented extracellularly again, is dissociated from FcRn at a pH returned to 7.4, and returns in the blood (FIG. 5B). Therefore, IgG has a half-life in blood as long as four weeks. IgG having mutation introduced therein to eliminate pH dependence is known to have a decreased half-life in blood. There is also a report on an example of extending a half-life in blood by enhancing its affinity at pH 6 without eliminating pH dependence.

Many of pH-dependent reactions are presumed to occur due to protonation and deprotonation of a histidine (His) residue, because an in vivo pH change is from about 5 to 7.4 and, among 20 amino acids, only the side chain of His has a pKa of 6. In practice, there is a report on an antibody that is prepared by introducing His into the CDR of an antibody and dissociats from an antigen in a pH-dependent manner (for example, Patent Document 1). This antibody binds strongly to an antigen in the blood of pH 7.4 and inhibits the function of the antigen, but when the antibody that binds to the antigen is introduced into an endosome at pH 6.0, it dissociates from the antigen in the endosome and the antibody is recycled, that is, released into the blood again. The document suggests that the antibody can therefore bind to a new antigen in the blood repeatedly.

A His-rich molecule is expected to acquire pH dependence, but preparation of such a molecule limits diversity of the sequence itself and therefore limits the possibility of creating a molecule undergoing pH-dependent binding. In addition, pH dependence attributable only to His is not always sufficient for a change in affinity due to a pH change.

CITATION LIST

Patent Document

Patent Document 1: JP2012-21004 A

DISCLOSURE OF THE INVENTION

Problem to be Solved by the Invention

If, for example, a peptide that strongly binds to FcRn at pH around 6 and does not bind thereto at around pH 7.4 is prepared and conjugated to a drug, there is a possibility of recycling the resulting drug through a pathway similar to that of an antibody and thereby extending its half-life in blood.

Further, there are areas different in pH from other areas in the living body, such as the areas around cancer cells that have an acidity higher than that in other areas. Therefore, if a peptide capable of binding to a target molecule in a pH dependent manner can be obtained, such areas can be targeted using such peptide.

An object of the present invention is therefore to provide molecules that bind to a target molecule in a pH dependent manner, a screening method for selecting such molecules, and the like.

Means for Solving the Problem

The present inventors have proceeded with an investigation with a view to achieving the above-mentioned object. Accordingly, it has been found that by preparing a library including peptides having a special amino acid that undergoes a change in the charge of its side chain even by a slight change in pH in vivo, binding the resulting library to a target molecule under a first pH condition, and dissociating the peptide from the target molecule under a second pH condition, a peptide having a pH-dependent binding property, more specifically, capable of binding to the target molecule at the first pH and not binding to the target molecule at the second pH can be obtained.

It has also been confirmed that a slight difference in pH causes a change of several ten times in the dissociation constant, for binding to the target molecule, of the peptides obtained by the above-mentioned screening method, leading to confirmation of the present invention.

In the present invention, there are provided:

[1] a screening method for selecting peptides that bind to a target molecule at a first pH and do not bind to the target molecule at a second pH, including:

a step of synthesizing a nucleic acid library in which nucleic acids respectively encode peptides containing at least one special amino acid that undergoes a pH-dependent change in the charge of the side chain thereof;

a step of using the nucleic acid library to express the peptides and prepare a peptide library;

a step of bringing the peptide library into contact with the target molecule and incubating them under the first pH condition and selecting peptides that bind to the target molecule; and a step of selecting, from the peptides that have bound to the target molecule, peptides that do not bind to the target molecule under the second pH condition;

[2] a screening method for selecting peptides that bind to a target molecule at a first pH and do not bind to the target molecule at a second pH, including:

a step of synthesizing a peptide-nucleic acid complex library in which peptides containing at least one special amino acid that undergoes a pH-dependent change in the charge of the side chain thereof have bound to nucleic acids encoding the peptides;

(a) a step of bringing the peptide-nucleic acid complex library into contact with the target molecule and incubating them under the first pH condition and selecting peptide-nucleic acid complexes that bind to the target molecule;

(b) a step of obtaining a nucleic acid library including nucleic acids of the selected peptide-nucleic acid complexes and preparing therefrom a peptide-nucleic acid complex library;

a step of carrying out the step (a) and the step (b) once or more;

a step of carrying out the step (a) again, eluting the peptide-nucleic acid complexes that have bound to the target molecule under the second pH condition, and identifying the peptides thus eluted;

[3] the method described in [1] or [2] above, wherein the amino acid that undergoes a pH-dependent change in the charge of the side chain thereof contains, in the side chain, a functional group that undergoes a change in protonated state at pH from 6 to 8;

[4] the method described in [1] or [2] above, wherein the amino acid that undergoes a pH-dependent change in the charge of the side chain thereof is selected from the followings:

tyrosine having at the 3-position or at the 3- and 5-positions thereof, $NO_2$, Cl, Br, I, $SO_2R$(R representing OH, $NH_2$, or Ar), COR(R representing OH, $NH_2$, Ar, $CF_3$, or $C_6F_5$), CN, $CF_3$, or $C_6F$ or N-substituted derivatives thereof;

arginine having at the Nw-position thereof, $NO_2$, $SO_2R$(R representing OH, $NH_2$, or Ar), COR(R representing OH, $NH_2$, Ar, $CF_3$, or $C_6F_5$), CN, $CF_3$, or $C_6F_5$, or N-substituted derivatives thereof;

phenylalanine having at the 2-, 3-, or 4-position thereof an amino group, or N-substituted derivatives thereof; and 2-pyridylalanine, 3-pyridylalanine, or 4-pyridylalanine, or N-substituted derivatives thereof:

[5] the method described in [1] or [2] above, wherein the amino acid that undergoes a pH-dependent change in the charge of the side chain thereof is selected from the following group:

[Chemical formula 1]

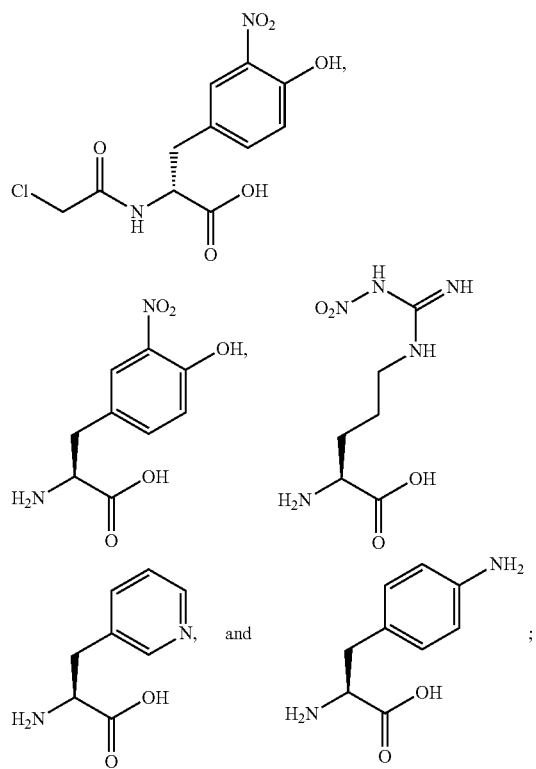

[6] the method described in any one of [1] to [5] above, wherein the peptides are each a cyclic peptide;

[7] a screening method for selecting peptides binding specifically to a protein expressed in cancer cells, wherein in the method described in any one of [1] to [6] above, the protein expressed in cancer cells is used as the target molecule, the first pH is made weakly acidic, and the second pH is made weakly basic;

[8] a screening method for selecting peptides to be recycled after pinocytosis, wherein in the method described in any one of [1] to [6] above, a neonatal Fc receptor (FcRn) is used as the target molecule, the first pH is made weakly acidic, and the second pH is made weakly basic;

[9] the method described in any one of [1] to [6] above, wherein the target molecule is an antigen or a cytokine receptor;

[10] A FcRn-binding peptide comprising any one of the following amino acid sequences or an amino acid sequence having one or several amino acid additions, substitutions, or deletions in the following amino acid sequences;

```
                                        (SEQ ID NO: 1)
F[Nty]LYN[Nna]GDPL[Nty]L, (SEQ ID NO: 2)
QSV[Nty]PDHWS[Pal], (SEQ ID NO: 3)
F[Nty]W[Nty]IWPKNY, (SEQ ID NO: 4)
VS[Nty]T[Pal][Nty]WYWD, (SEQ ID NO: 5)
[Pal]NFGPLWSKLS[Nna],
and (SEQ ID NO: 6)
LKS[Nty]LSWVYKS
```

[wherein, Nty represents 3-nitro-L-tyrosine, Nna represents Nw-nitro-L-arginine, and Pal represents 3-pyridyl-L-alanine];

[11] A FcRn-binding Peptide comprising any one of the following amino acid sequences or an amino acid sequence having one or several amino acid additions, substitutions, or deletions in the following amino acid sequences;

```
                                        (SEQ ID NO: 7)
[AcD-Nty]F[Nty]LYN[Nna]GDPL[Nty]LC, (SEQ ID NO: 8)
[AcD-Nty]QSV[Nty]PDHWS[Pal]C, (SEQ ID NO: 9)
[AcD-Nty]F[Nty]W[Nty]IWPKNYC, (SEQ ID NO: 10)
[AcD-Nty]VS[Nty]T[Pal][Nty]WYWDC, (SEQ ID NO: 11)
[AcD-Nty][Pal]NFGPLWSKLS[Nna]C,
and (SEQ ID NO: 12)
[AcD-Nty]LKS[Nty]LSWVYKSC
```

[wherein, $^{Ac}$D-Nty represents N-acetyl-3-nitro-D-tyrosine, Nty represents 3-nitro-L-tyrosine, Nna represents Nω-nitro-L-arginine, Pal represents 3-pyridyl-L-alanine and each of the peptides may be circularized by a thioether bond between the acetyl group of $^{Ac}$D-Nty and the cysteine residue];

[12] a complex between a peptide selected by the method described above in any one of [1] to [9] or a peptide described in [10] or [11] above and a drug; and

[13] a kit for carrying out the screening method described in any one of [1] to [9] above.

Effect of the Invention

The screening method of the invention makes it possible to identify peptides that undergoes a large change in dissociation constant in a reaction with a desired target molecule even with a slight difference in pH.

For example, when FcRn is used as the target molecule, even when the peptide obtained by the invention or a complex containing such peptide is brought in a cell by pinocytosis, there is a high possibility of it being released again in the blood by exocytosis. This permits extension of the half-life in blood.

The peptide obtained by the invention or a complex containing such peptide can be sent specifically to a tissue, organ, or the like showing a pH different from that therearound in vivo.

EMBODIMENT FOR CARRYING OUT THE INVENTION

Figure 1:
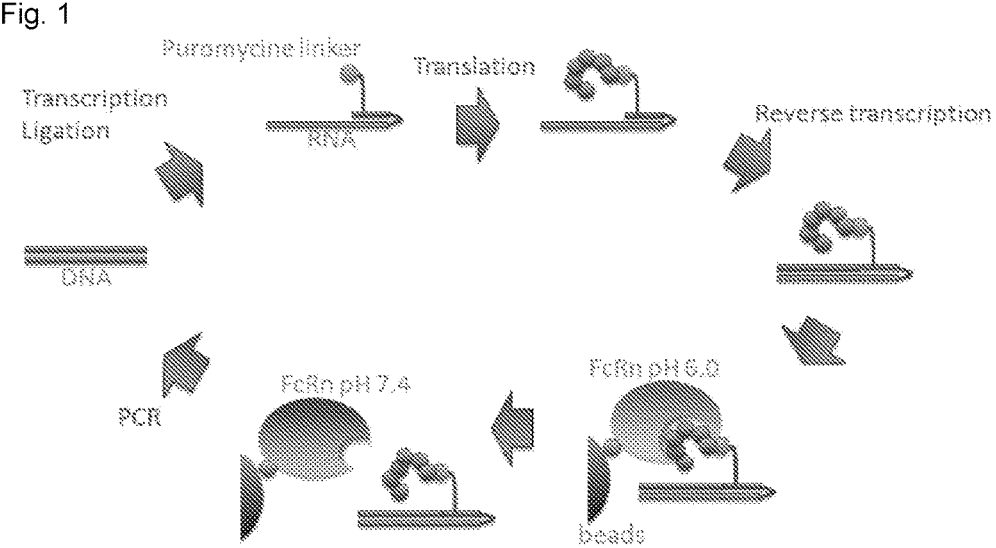
FIG. 1 is a conceptual diagram for describing mRNA display carried out in Examples.

A screening method according to a first embodiment of the present invention is a method for selecting peptides that bind to a target molecule at a first pH and do not bind to the target molecule at a second pH, including:

synthesizing a nucleic acid library in which nucleic acids encode peptides each containing at least one special amino acid that undergoes a pH-dependent change in the charge of the side chain thereof, respectively;

using the nucleic acid library to express the peptides and prepare a peptide library;

bringing the peptide library into contact with the target molecule and incubating them under the first pH condition and selecting peptides that bind to the target molecule; and eluting the peptides bound to the target molecule under the second pH condition and identifying the peptides thus eluted.

Although the target molecule is not particularly limited herein, for example, proteins and peptides can be used. Examples of the target molecule include FcRn, various antigens, and various receptors, and fragments thereof.

The term "library" as used herein means a collection containing two or more nucleic acids or peptides wholly or partly having a random sequence.

The term "nucleic acid" as used herein embraces DNA, RNA, and DNA/RNA chimera and it may also embrace artificial bases such as PNA (peptide nucleic acid) and LNA (locked nucleic acid). The term "expression" is used herein as either a term "transcription" in which an RNA polymerase produces mRNA according to the sequence of DNA or as a term "translation" in which a peptide or a protein is synthesized according to the sequence of mRNA and those skilled in the art can judge the meaning of the term from the context.

In the present specification, the first pH and the second pH may be any pHs insofar as they are different from each other. The first pH may be higher than the second pH or the first pH may be lower than the second pH. Those skilled in the art may carry out the screening method of the present invention based on the first pH and the second pH selected according to the object.

For example, when the target molecule is FcRn, the first pH may be set at from about 5.5 to 6 equal to that in the endosome and the second pH may be set at about 7.4 equal to that in the plasma. When identifying a peptide that specifically binds to the target molecule around cancer cells, the first pH may be made weakly acidic (for example, pH from 6.3 to 6.8) and the second pH may be made weakly basic (for example, pH from 7.2 to 7.5).

Additional examples of the pH combination include a combination of the first pH from about 4.0 to 6.5 and the second pH from about 6.7 to 10.0, a combination of the first pH from about 6.7 to 10.0 and the second pH from about 4.0 to 6.5, a combination of the first pH from about 5.5 to 6.5 and the second pH from about 7.0 to 8.0, and a combination of the first pH from about 7.0 to 8.0 and the second pH from about 5.5 to 6.5.

In the term "bind at the first pH and do not bind at the second pH" used herein, the terms "bind" and "do not bind" mean a relative state and they not only mean that all the molecules in the system bind to the target molecule or none of the molecules bind to the target molecule. The case where a peptide that bind to the target molecule is predominant at the first pH and a peptide that does not bind to the target molecule is predominant at the second pH, or the case where a dissociation constant for binding to the target molecule is overwhelmingly smaller at the first pH than at the second pH also corresponds to the state described as "bind at the first pH and do not bind at the second pH".

In the screening method according to the first embodiment of the present invention, first, a step of synthesizing a nucleic acid library is carried out, in which nucleic acids encode peptides each containing at least one special amino acid that undergoes a pH-dependent change in the charge of the side chain thereof, respectively.

The term "amino acid" is used herein in the broadest meaning and it embraces, as well as natural amino acids, artificial amino acid mutants and derivatives. Examples of the amino acid used herein include natural protein L-amino acids; D-amino acids; chemically modified amino acids such as amino acid mutants and derivatives; natural non-protein amino acids such as norleucine, β-alanine, and ornithine; N-substituted amino acids; and chemically synthesized compounds having characteristics of amino acids known to the industry. Examples of the non-natural amino acids include α-methylamino acids (such as α-methylalanine), D-amino acids, histidine-like amino acids (such as β-hydroxy-histidine, homohistidine, α-fluoromethyl-histidine, and α-methyl-histidine), amino acids ("homo"amino acids) having, in the side chain thereof, extra methylene, and amino acids (such as cysteic acid) whose carboxylic acid functional amino group in the side chain has been substituted with a sulfonic acid group.

The amino acids are each represented herein by conventionally used single letter code or three letter code. The amino acids represented by single letter code or three letter code sometimes include mutants or derivatives thereof.

In the present specification, non-protein amino acids, non-natural amino acids, and artificial amino acids are collectively called "special amino acids".

The term "special amino acid that undergoes a pH-dependent change in the charge of the side chain thereof" is used herein in the broadest meaning and it means a special amino acid whose side chain is protonated, deprotonated, anionized, or deanionized in response to a slight change in pH. Examples include amino acids having, in a side chain thereof, an amino group or a nitrogen atom, protonated due to a reduction in pH, and deprotonated due to an increase in pH; and amino acids having, as a side chain thereof, a hydroxyl group which is anionated due to an increase in pH and deanionated due to a reduction in pH. As the "special amino acid that undergoes a pH-dependent change in the charge of the side chain thereof", amino acids having a side chain with a pKa of from about 4 to 10 (preferably a pKa of from 5 to 9) or amino acids having a side chain with a pKb of from about 6 to 7.4 can be used. Amino acids (including N-substituted amino acids) having a pH around 7, that is, from about 6 to 8 and having, as a side chain thereof, a functional group undergoing a change in protonated state may be used.

Non-limiting examples of such an amino acid include:

tyrosine having at the 3-position or at the 3- and 5-positions thereof, $NO_2$, Cl, Br, I, $SO_2R$(R representing OH, $NH_2$, Ar, or the like), COR(R representing OH, $NH_2$, Ar, $CF_3$, $C_6F_5$, or the like), CN, $CF_3$, $C_6F$, or the like, or N-substituted derivatives thereof;

arginine having at the Nω-position thereof, $NO_2$, $SO_2R$(R representing OH, $NH_2$, Ar or the like), COR(R representing OH, $NH_2$, Ar, $CF_3$, $C_6F_5$, or the like), CN, $CF_3$, $C_6F_5$ or the like, or N-substituted derivatives thereof;

phenylalanine having at the 2-, 3-, or 4-position thereof an amino group, or N-substituted derivatives thereof; and 2-pyridylalanine, 3-pyridylalanine, or 4-pyridylalanine, or N-substituted derivatives thereof.

Examples of such amino acids include:

[Chemical formula 2]

(I)

(II)

(III)

(IV)

(V)

Compound (I): N-chloroacetyl-3-nitro-D-tyrosine ($^{ClAc}$D-Nty)
Compound (II): 3-nitro-L-tyrosine (Nty)
Compound (III): Nω-nitro-L-arginine (Nna)
Compound (IV): 3-pyridyl-L-alanine (Pal)
Compound (V): 4-amino-L-phenylalanine (Aph)

As a result of anionization or protonation of the circled hydroxyl group, amino group, or nitrogen atom, these amino acids undergo a change in the charge of a side chain thereof due to a slight change in pH.

A nucleic acid encoding a peptide containing at least a special amino acid that undergoes a pH-dependent change in the charge of the side chain thereof can be obtained by assigning a codon encoding the special amino acid by "genetic code reprogramming" and creating a nucleic acid containing at least one such codon.

A description will next be made on the genetic code reprogramming.

In vivo translation, a triplet of three bases of mRNA as one codon designates one amino acid and a peptide corresponding to the triplets is synthesized. At this time, correspondence between a codon and an amino acid is performed in the following two stages. (i) To the terminal of tRNA, an aminoacyl-tRNA synthetase (ARS) couples an amino acid corresponding thereto. (ii) Due to pairing of a tRNA anticodon and an mRNA codon corresponding thereto, an amino acid on the tRNA is polymerized and a peptide is synthesized according to the information of mRNA.

Such a corresponding relationship between a codon and an anticodon is almost determined universally and any one of 20 amino acids is assigned to 64 kinds of codons. The following is a universal genetic code table.

TABLE 1

|   | U |   | C |   | A |   | G |   |
|---|---|---|---|---|---|---|---|---|
|   | Codon | Amino acid | Codon | Amino acid | Codon | Amino acid | Codon | Amino acid |
| U | UUU | Phenylalanine | UCU | Serine | UAU | Tyrosine | UGU | Cysteine | U |
|   | UUC | Phenylalanine | UCC | Serine | UAC | Tyrosine | UGC | Cysteine | C |
|   | UUA | Leucine | UCA | Serine | UAA | Stop | UGA | Stop | A |
|   | UUG | Leucine | UCG | Serine | UAG | Stop | UGG | Tryptophan | G |
| C | CUU | Leucine | CCU | Proline | CAU | Histidine | CGU | Arginine | U |
|   | CUC | Leucine | CCC | Proline | CAC | Histidine | CGC | Arginine | C |
|   | CUA | Leucine | CCA | Proline | CAA | Glutamine | CGA | Arginine | A |
|   | CUG | Leucine | CCG | Proline | CAG | Glutamine | CGG | Arginine | G |
| A | AUU | Isoleucine | ACU | Threonine | AAU | Asparagine | AGU | Serine | U |
|   | AUC | Isoleucine | ACC | Threonine | AAC | Asparagine | AGC | Serine | C |
|   | AUA | Isoleucine | ACA | Threonine | AAA | Lysine | AGA | Arginine | A |
|   | AUG | Methionine | ACG | Threonine | AAG | Lysine | AGG | Arginine | G |
| G | GUU | Valine | GCU | Alanine | GAU | Aspartic acid | GGU | Glycine | U |
|   | GUC | Valine | GCC | Alanine | GAC | Aspartic acid | GGC | Glycine | C |
|   | GUA | Valine | GCA | Alanine | GAA | Glutamic acid | GGA | Glycine | A |
|   | GUG | Valine | GCG | Alanine | GAG | Glutamic acid | GGG | Glycine | G |

Genetic code reprogramming can be achieved by binding, to an arbitrary tRNA, an arbitrary amino acid different from a natural one and using it in an expression system using a cell-free translation system or the like.

Described specifically, "genetic code reprogramming" is performed so that a codon can designate an amino acid different from that shown in the above table by using an aminoacylated tRNA obtained by binding a desired amino acid to an arbitrary tRNA.

When a cell-free translation system is used for genetic code reprogramming, constituting components of the cell-free translation system can be arbitrarily selected according to the purpose. For example, when a specific amino acid is removed from the translation system, the codon corresponding to the amino acid becomes a vacant codon. A desired amino acid is linked to a tRNA having an anticodon complementary to the vacant codon and when translation is performed with it, the amino acid is coded by the codon, resulting in translation of a peptide having the desired amino acid introduced therein instead of the removed amino acid.

As a method of binding an arbitrary amino acid to an arbitrary tRNA, for example, an artificial aminoacylation RNA catalyst "flexizyme" can be used.

Flexizyme is an artificial RNA catalyst (an RNA catalyst having an aminoacyl-tRNA synthetase-like activity) capable of linking (acylating) an arbitrary amino acid or hydroxy acid to an arbitrary tRNA. For example, those described in the following documents are known: H. Murakami, H. Saito, and H. Suga, (2003), "A Versatile tRNA Aminoacylation Catalyst Based on RNA" Chemistry & Biology, Vol. 10, 655-662; H. Murakami, D. Kourouklis, and H. Suga, (2003), "Using a solid-phase ribozyme aminoacylation system to reprogram the genetic code" Chemistry & Biology, Vol. 10, 1077-1084; H. Murakami, A. Ohta, H. Ashigai, H. Suga (2006) "The flexizyme system: a highly flexible tRNA aminoacylation tool for the synthesis of normatural peptides" Nature Methods 3, 357-359; N. Niwa, Y. Yamagishi, H. Murakami, H. Suga (2009) "A flexizyme that selectively charges amino acids activated by a water-friendly leaving group" Bioorganic & Medicinal Chemistry Letters 19, 3892-3894; and WO2007/066627 "Multi-purpose acylation catalyst and use thereof"). Flexizyme is also known as original flexizyme (Fx) and modified ones such as dinitrobenzyl flexizyme (dFx), enhanced flexizyme (eFx), and aminoflexizyme (aFx).

Flexizyme, for example, enables the above-mentioned special amino acid that undergoes a pH-dependent change in the charge of the side chain thereof to link to a tRNA.

As a method of linking an arbitrary amino acid to an arbitrary tRNA, a method using chemical amino acylation or a mutant protein enzyme can also be used.

More specifically, for example, by removing methionine from the system, AUG becomes a vacant codon. Then, a DNA containing AUG at least one random position is synthesized and transcribed to obtain an mRNA. On the other hand, by linking $^{ClAc}$D-Nty to a tRNA having an anticodon corresponding to codon AUG and translating the mRNA by using it, a peptide containing $^{ClAc}$D-Nty at least one random position can be obtained.

Therefore, in order to synthesize a nucleic acid library in which nucleic acids respectively encode peptides containing at least one special amino acid that undergoes a pH-dependent change in the charge of the side chain thereof, it is only necessary, when the nucleic acid is a DNA, to assign a codon encoding the special amino acid that undergoes a pH-dependent change in the charge of the side chain thereof and synthesize a DNA containing at least one such codon at random. When the nucleic acid is an RNA, on the other hand, the DNA library may be transcribed to synthesize the library. Synthesis and transcription of the DNA can be performed in a known manner.

In the screening method according to the first embodiment of the present invention, the nucleic acid library is then expressed. As an expression system, a cell-free translation system is preferably used.

The "cell-free translation systems" used herein contains, for example, ribosome protein, aminoacyl tRNA synthetase (ARS), ribosome RNA, amino acid, energy source (GTP, ATP, or the like), tRNA, amino acid, translation initiation factor (IF), elongation factor (EF), release factor (RF), ribosome recycling factor (RRF), and other factors necessary for translation. An *Escherichia coli* extract or wheat germ extract may be used in order to enhance an expression efficiency. A rabbit erythrocyte extract or an insect cell extract may be used instead. For example, as a system using an *Escherichia coli* ribosome, technologies described in the following documents are known: H. F. Kung, B. Redfield, B. V. Treadwell, B. Eskin, C. Spears, and H. Weissbach (1977) "DNA-directed in vitro synthesis of beta-galactosidase. Studies with purified factors" The Journal of Biological Chemistry Vol. 252, No. 19, 6889-6894; M. C. Gonza, C. Cunningham, and R. M. Green (1985) "Isolation and point of action of a factor from *Escherichia coli* required to reconstruct translation" Proceeding of the National Academy of Sciences of the United States of America, Vol. 82, No. 6, 1648-1652; M. Y. Pavlov and M. Ehrenberg (1996), "Rate of translation of natural mRNAs in an optimized in vitro system" Archives of Biochemistry and Biophysics Vol. 328, No. 1, 9-16; Y. Shimizu, A. Inoue, Y. Tomari, T. Suzuki, T. Yokogawa, K. Nishikawa, and T. Ueda (2001), "Cell-free translation reconstituted with purified components" Nature Biotechnology, Vol. 19, No. 8, 751-755; H. Ohashi, Y. Shimizu, B. W. Ying, and T. Ueda (2007) "Efficient protein selection based on ribosome display system with purified components" Biochemical and Biophysical Research Communications Vol. 352, No. 1, 270-276.

At this time, by adding a conjugate of a special amino acid undergoing a pH-dependent change in the charge of a side chain thereof and a tRNA having an anticodon complementary to a codon encoding the special amino acid, a peptide library containing at least one special amino acid that undergoes a pH-dependent change in the charge of the side chain thereof can be obtained.

The term "peptide" as used herein means two or more amino acids bound through a peptide bond. Although the number of the amino acids is not particularly limited, a peptide may be composed of, for example, from 3 amino acids to 50 amino acids or from 5 amino acids to 30 amino acids.

In addition, the number of the special amino acids contained in each of the peptides of a peptide library and undergoing a pH-dependent change in the charge of a side chain thereof is also not particularly limited, but examples include two or more, three or more, and five or more. It may be set at, for example, 10% or more, 20% or more, or 30% or more of the number of the amino acids of the peptide as a whole.

The term "peptide" as used herein embraces a cyclic peptide. The term "cyclic peptide" means a peptide which has therein two amino acids bound to each other and has been wholly or partially cyclized.

A peptide, when cyclized, is presumed to have improved protease resistance or have enhanced rigidity, thereby having improved membrane permeability or improved affinity with a target protein. For example, a peptide designed to contain two or more cysteine residues can form a cyclic structure via a disulfide bond after translation. Cyclization can also be achieved by synthesizing a peptide having, at an N terminal thereof, a chloroacetyl group by a genetic code reprogramming technology and placing a cysteine residue in the peptide according to the method of Goto et al (Y. Goto et al. ACS Chem. Biol. 3, 120-129 (2008)). After translation, a mercapto group spontaneously performs nucleophilic attack on the chloroacetyl group, leading to cyclization of the peptide via a thioether bond. Cyclization may also be achieved by placing, in the peptide, a combination of other amino acids that are bound to each other to form a ring by genetic code reprogramming technology.

In the screening method according to the first embodiment of the present invention, a step of bringing the peptide library into contact with the target molecule under the first pH condition and selecting peptides that bind to the target molecule and a step of selecting, from the peptides which have bound to the target molecule, peptides that do not bind to the target molecule under the second pH condition are carried out next.

In these steps, conditions other than pH can be determined as needed by those skilled in the art depending on the target molecule. The step of selecting peptides that bind to the target molecule and the step of selecting peptides that do not bind to it are preferably conducted under the same conditions except for the pH condition.

The step of selecting peptides that bind to a target molecule can be performed as needed by those skilled in the art in a known manner. For example, it can be performed by, after immobilizing the target molecule to a solid-phase substrate and bringing it into contact with the peptide library, recovering the solid-phase substrate together with the peptides that have bound to the target molecule or by washing the surface of the solid-phase substrate with an appropriate buffer to capture only the peptides that have bound to the target molecule on the surface of the solid-phase substrate.

In this case, the step of selecting peptides that do not bind to a target molecule can be performed by eluting the surface of the solid-phase substrate under the second pH condition and identifying the peptides released from the target molecule under the second pH condition.

The "solid-phase substrate" used herein is not particularly limited insofar as it is a substrate onto which a target molecule can be immobilized. Examples include a microtiter plate made of glass, a metal, a resin, or the like, a plate, beads, a nitrocellulose membrane, a nylon membrane, and a PVDF membrane. The target molecule can be immobilized on to such a solid-phase substrate in a known manner.

The elution step, identification of peptides thus eluted, and the like can be carried out by those skilled in the art in a known manner.

The step of selecting peptides that bind to a target molecule and peptides that do not bind to the target molecule can be carried out also by determining the binding strength between the target molecule and each peptide at the first pH and the second pH.

The binding strength between the target molecule and each peptide can be determined using any method for analyzing an interaction between proteins. For example, it may be determined from a dissociation constant for binding. The dissociation constant can be determined from Biacore (GE healthcare) making use of surface plasmon resonance or FACS.

The peptides that bind to a target molecule and the peptides that do not bind to the target molecule can be designated as peptides having a dissociation constant for binding to the target molecule different from each other by 2 times or more, 10 times or more, 20 times or more, or 40 times or more.

A screening method according to a second embodiment of the present invention will next be described. The method according to the second embodiment employs various display technologies making use of a cell-free translation system or the like. It includes:

synthesizing a peptide-nucleic acid complex library in which peptides containing at least one special amino acid that undergoes a pH-dependent change in the charge of the side chain thereof have bound to nucleic acids encoding the peptides, respectively;

(a) bringing the peptide-nucleic acid complex library into contact with the target molecule under the first pH condition and selecting peptide-nucleic acid complexes that bind to the target molecule;

(b) obtaining a nucleic acid library including nucleic acids of the selected peptide-nucleic acid complexes and preparing therefrom a peptide-nucleic acid complex library;

carrying out the step (a) and the step (b) once or more; and carrying out the step (a) again, eluting under the second pH condition the peptide-nucleic acid complexes bound to the target molecule and identifying the eluted peptides. The terms similar to those in the first embodiment have the same meanings so that an overlapping description is omitted.

In the second embodiment, first, a peptide-nucleic acid complex library in which peptides containing at least one special amino acid that undergoes a pH-dependent change in the charge of the side chain thereof have bound to nucleic acids encoding the peptides, respectively is synthesized. A step of synthesizing a nucleic acid library encoding peptides containing at least one special amino acid that undergoes a pH-dependent change in the charge of the side chain thereof is carried out by a method equivalent to that of the first embodiment.

Then, a peptide-nucleic acid complex library in which said nucleic acids have bound to peptides, respectively, is prepared using a method suited for various display methods. The term "display method" as used herein means a technology of correlating a DNA or mRNA (genotype) and a peptide (phenotype) while using a cell-free translation system, phage, or the like. Examples include, but not limited to, mRNA display (Nemoto, N. et al, (1997) FEBS Lett., 414, 405-408; Roberts, R. W. & Szostak, J. W. (1997) Proc. Natl. Acad. Sci. USA, 94, 12297-12302), ribosome display (Mattheakis, L. C. et al., (1994) Proc. Natl. Acad. Sci. USA, 91, 9022-9026; Hanes, J. and Plueckthun, A. (1997) Proc. Natl. Acad. Sci. USA, 94, 4937-4942), DNA display, RAPID display (WO2011/049157), phage display (Science. 1985 Jun. 14; 228(4705):1315-7.), bacterial display (Proc Natl Acad Sci USA, 1993 Nov. 15; 90(22): 10444-8.), Mammalian cell display (Proc Natl Acad Sci USA. 2008 Sep. 23; 105(38):14336-41.), and Yeast display (Nat. Biotechnol. 1997, Jun., 15(6):553-7.). In the peptide-nucleic acid complex library, nucleic acids may bind to peptides directly or via a linker or another molecule (for example, ribosome). Those skilled in the art can select a proper binding method according to the display method employed.

When mRNA display is used as the display method, after preparation of the mRNA library by the above-mentioned method, puromycin is bound to the 3' end of each mRNA to prepare a puromycin-bound mRNA library. Binding of puromycin to the 3' end of each mRNA can be performed in a known manner. Each mRNA and puromycin may be bound to each other via a spacer.

Next, a peptide-mRNA complex library can be prepared by expressing the peptides in a cell-free translation system by using the puromycin-bound mRNA library. When a cell-free translation reaction is performed using, as a template, an mRNA having puromycin bound to the 3' end thereof, puromycin binds to a peptide chain at a P site of ribosome to form peptide-mRNA complexes.

When ribosome display is used as the display method, an mRNA library is prepared by using the above-mentioned method while constituting the library so that each mRNA lacks a stop codon. When the mRNA has thereon a stop codon, dissociation between the translated peptides and a ribosome occurs by the catalytic action of a dissociation factor group that binds to the stop codon. No dissociation between the ribosome and mRNA however occurs in the absence of the stop codon, leading to preparation of mRNA-ribosome-peptide complexes.

As the display method, DNA display that makes use of DNA-peptide complexes may be employed. Examples of the DNA display include STABLE method (Doi, N. and Yanagawa, H. (1999) FEBS Lett., 457, 227-230). In this method, after preparation of a DNA library encoding a fusion protein between a peptide containing at least one special amino acid that undergoes a pH-dependent change in the charge of the side chain thereof and streptavidin, each DNA is labeled with biotin and expressed in a compartment formed from a W/O emulsion. Then, streptavidin and biotin bind to each other to form complexes between the DNA and expressed peptide. As DNA display, CIS display (Proc. Natl. Acad Sci USA. 2004 Mar. 2; 101(9): 2806-10), Covalent Antibody Display (Nucleic Acids Res. 2005; 33(1): e10.), SNAP Display (Methods Mol. Biol., 2012; 805:101-11.) or the like can be used. Those skilled in the art can obtain DNA-peptide complexes by using these display methods.

As the display method, RAPID display may be used. RAPID display is a method using a linker having, at one end thereof, a single-stranded region hybridized with the 3' end bases of an mRNA encoding a peptide and, at the other end, a peptide acceptor region containing a group linkable to a translation product by a peptide transfer reaction. The peptide acceptor region has a structure in which an amino acid has been ester-bonded to an oligo RNA having a base sequence ACCA.

In this case, upon preparing a DNA library encoding peptides each containing at least one special amino acid that undergoes a pH-dependent change in the charge of the side chain thereof, a region complementary to the single-stranded region of the linker is provided downstream of the peptide encoding region. When such a DNA library is transcribed and translated in a cell-free system in the presence of the linker, the single-stranded region of the linker hybridizes to the 3' end of the mRNA and the other end of the linker binds to the C-terminal amino acid of the translation product, which results in formation of mRNA-linker-peptide complexes.

Those skilled in the art can prepare a peptide-nucleic acid complex library in which nucleic acids and peptides have bound to each other by making use of any display method capable of establishing genotype-phenotype correlation as well as the above-mentioned methods.

The peptide-nucleic acid complex library thus obtained is brought into contact with the target molecule under the first pH condition, followed by incubation. Then, peptide-nucleic acid complexes that bind to the target molecule are selected. This step will hereinafter be called step (a). This step can be performed in various known manners by those skilled in the art. For example, it can be achieved by bringing the peptide-nucleic acid complex library into contact with the target molecule immobilized onto a solid-phase substrate in advance, incubating, and then recovering the solid-phase substrate together with the complexes; or washing the surface of the solid-phase substrate to separate only the complexes that have bound to the target molecule.

Alternatively, it can be achieved by binding biotin to the target molecule in advance, bringing the biotinated target molecule into contact with the peptide-nucleic acid complex library in a liquid phase, adding streptavidin magnetic beads to bind biotin and streptavidin to each other, and recovering the magnetic beads by using a magnet.

The step (a) is followed by the step (b) of obtaining a nucleic acid library including nucleic acids of the selected peptide-nucleic acid complexes and preparing therefrom a peptide-nucleic acid complex library.

A method of preparing a peptide-nucleic acid complex library from the nucleic acid library can be performed, as described above, by modification of nucleic acids as needed by those skilled in the art, preparation of a necessary linker, and translation in a cell-free translation system or the like.

For example, when mRNA display is used, first, a step of binding puromycin to the 3' end of each mRNA to prepare a puromycin-bound mRNA library. More specifically, the mRNA of the selected peptide-mRNA complex group is reverse-transcribed to obtain a cDNA group and the resulting cDNA group is transcribed to obtain an mRNA library again. Then, puromycin is bound to the 3' end of each mRNA and as a result, a puromycin-bound mRNA library can be prepared. The resulting puromycin-bound mRNA library can be translated in a cell-free system into a peptide-mRNA complex library.

After a set of the steps (a) and (b) is performed once or more to sufficiently concentrate the peptides that bind to the target molecule, the step (a) is performed again and peptide-nucleic acid complexes that have bound to the target molecule are eluted under the second pH condition. The number of the set of the steps (a) and (b) is not particularly limited and the set of the steps is performed until the peptides that bind to the target molecule are concentrated sufficiently. For example, it is performed three times, five times, seven times, or the like.

More specifically, for example, when the target molecule is immobilized onto beads, the resulting beads are recovered in the step (a) and peptide-mRNA complexes that have bound to the target molecule are selected. Then, peptide-mRNA complexes are eluted from the beads with a buffer of the second pH condition.

By identifying such peptides, peptides that bind to the target molecule at the first pH and do not bind thereto at the second pH can be selected.

When mRNA display is used as the above-mentioned display method, upon binding puromycin to the 3'-end of an mRNA, a DNA fragment complementary to a portion of the 3' end of the mRNA may be linked to the 3' end of the mRNA according to the method of JP 2002-291491 A and puromycin may be bound to the 3' end of the DNA fragment.

In this case, it is also possible to use, after a step of expressing the peptides in a cell-free translation system by using the puromycin-bound mRNA library to prepare the peptide-mRNA complex library, a reverse transcriptase to synthesize a DNA complementary to a single-stranded portion of the mRNA so as to extend the DNA fragment. This enables formation of a hybrid between the mRNA of the peptide-mRNA complex library and the DNA and as a result, the step (a) can be performed more stably.

In this case, in the step (b), a double-stranded DNA is obtained from the selected peptide-mRNA complexes by PCR and is then transcribed to obtain the RNA. Then, to the 3' end of the resulting mRNA, a DNA fragment complementary to a portion of the 3' end of the mRNA is ligated, followed by binding puromycin to the ligation product to obtain a puromycin-bound mRNA library.

The peptides obtained by the above-mentioned screening method are used for various purposes based on its property of binding to the target molecule at the first pH and not binding to the target molecule at the second pH.

For example, when a target molecule is a protein expressed in both cancer cells and normal cells, peptides obtained by adjusting the first pH to weakly acidic (for example, from pH 6.3 to 6.8) and the second pH to weakly basic (for example, from pH 7.2 to 7.5) can bind to the target molecule only at an acidic region around cancer cells and cannot bind to the target molecule around normal cells. If such peptides are bound to an anticancer agent in advance, the resulting anticancer agent can be delivered selectively to the region around cancer cells.

Peptides obtained by using FcRn as a target molecule and setting the first pH at from about 5.5 to 6 and the second pH at about 7.4 can bind to FcRn when brought into a high-acidity endosome by pinocytosis. Then, they are exocytosed without being degraded in a lysosome, leading to dissociation from FcRn in the blood having a pH of about 7.4. Therefore, when such peptide are bound to a drug, for example, a protein drug in advance, the resulting drug is not degraded even by pinocytosis and is released into the blood again and recycled. As a result, the drug can have an extended half-life in blood.

FcRn is known to be expressed in the airway epithelial cells and it is reported that a protein pharmaceutical is transpulmonarily administered through pH-dependent interaction with this FcRn (for example, Bitonti, A. J. & Dumont, J. A. Advanced Drug Delivery Reviews 58, 1106-1118 (2006).; Liebert, M. A. et al. Journal of Aerosol Medicine 18, 294-303 (2005); Vllasaliu, D. et al. Journal of Controlled Release 1-9 (2011). doi: 10.1016/j. jconrel. 2011.12.009). Accordingly, when peptides obtained using FcRn as the target molecule are bound to a drug such as protein drug in advance, the drug can be administered transpulmonarily.

Some of main metabolic pathways of an antibody are dependent on a membrane antigen. In this case, the antibody is endocytosed while being bound to the membrane antigen and then degraded in a lysosome together with the membrane antigen. Similarly, a cytokine also has a metabolic pathway in which the cytokine is degraded while being bound to a receptor (for example, Igawa, T. et al. Nature Biotechnology 28, 1203-1207 (2010).; Chaparro-riggers, J. et al. Journal of Biological Chemistry 1-15 (2012).doi: 10.1074/jbc.M111.319764; Sarkar, C. A. et al. Nature Biotechnology 20, (2002).; JP 2012-21004 A, JP 2010-536384 T, and JP 2004-508044 T).

There is a possibility of avoiding degradation if a peptide dissociable from a membrane antigen or cytokine receptor in a pH dependent manner can be obtained by the method of the present invention while using the membrane antigen or cytokine receptor as a target molecule.

No particular limitation is imposed on a drug to be bound to the peptide and it may be a low molecular compound, high molecular compound, nucleic acid, protein, peptide, or the like. A peptide-drug complex is prepared in a known manner. When the drug is a peptide or protein, the complex may be expressed as a fusion protein or the drug and the peptide may be bound to each other via a linker. Such a complex may be administered after formulated as needed.

The present invention also embraces peptides comprising the following amino acid sequence or an amino acid sequence having one or several amino acid additions, substitutions, or deletions in the following amino acid sequence, and binding to FcRn in a pH dependent manner according to the present invention:

F[Nty]LYN[Nna]GDPL[Nty]L, (SEQ ID NO: 1)

QSV[Nty]PDHWS[Pal], (SEQ ID NO: 2)

F[Nty]W[Nty]IWPKNY, (SEQ ID NO: 3)

VS[Nty]T[Pal][Nty]WYWD, (SEQ ID NO: 4)

[Pal]NFGPLWSKLS[Nna], and (SEQ ID NO: 5)

LKS[Nty]LSWVYKS (SEQ ID NO: 6)

[wherein, Nty represents 3-nitro-L-tyrosine, Nna represents Nω-nitro-L-arginine, and Pal represents 3-pyridyl-L-alanine].

These peptides may have, at the N terminal and C terminal thereof, [$^{Ac}$D-Nty] and C, respectively, as follow:

[$^{Ac}$D-Nty]F[Nty]LYN[Nna]GDPL[Nty]LC, (SEQ ID NO: 7)

[$^{Ac}$D-Nty]QSV[Nty]PDHWS[Pal]C, (SEQ ID NO: 8)

[$^{Ac}$D-Nty]F[Nty]W[Nty]IWPKNYC, (SEQ ID NO: 9)

[$^{Ac}$D-Nty]VS[Nty]T[Pal][Nty]WYWDC, (SEQ ID NO: 10)

[$^{Ac}$D-Nty][Pal]NFGPLWSKLS[Nna]C, and (SEQ ID NO: 11)

[$^{Ac}$D-Nty]LKS[Nty]LSWVYKSC (SEQ ID NO: 12)

[wherein, $^{Ac}$D-Nty represents N-acetyl-3-nitro-D-tyrosine, Nty represents 3-nitro-L-tyrosine, Nna represents Nω-nitro-L-arginine, and Pal represents 3-pyridyl-L-alanine; and each peptide may form a ring through a thioether bond between the acetyl group of $^{Ac}$D-Nty and the cysteine residue].

The term "one or several amino acid additions, substitutions, or deletions" as used herein does not limit their number or position insofar as the peptide thus obtained binds to FcRn. They may be from one to five, for example, two, three, or four amino acid additions, substitutions, or deletions and these additions, substitutions, or deletions may occur at the N terminal or the C terminal, or at a position other than the terminal. When the amino acid sequence has two or more additions, substitutions, or deletions, they may be continuous or discontinuous.

The C terminal of the peptide may be OH, $NH_2$, ester, or the like, and PEG, an alkyl chain, piperidine, or the like may bind to it.

A polypeptide of the present invention embraces salts of the polypeptide. As the salt of the polypeptide, salts of a physiologically acceptable base or acid are used. Examples include addition salts of inorganic acids (such as hydrochloric acid, hydrobromic acid, hydroiodic acid, sulfuric acid, and phosphoric acid), addition salts of organic acids (such as p-toluenesulfonic acid, methanesulfonic acid, oxalic acid, p-bromophenylsulfonic acid, carboxylic acid, succinic acid, citric acid, benzoic acid, and acetic acid), inorganic bases (such as ammonium hydroxide and alkali or alkaline earth metal hydroxides, carbonates, and bicarbonates), and addition salts of amino acids.

The polypeptide of the present invention may be modified, for example, phosphorylated, methylated, acetylated, adenylylated, ADP-ribosylated, or glycosylated insofar as it achieves the object of the present invention. It may be obtained by fusing with another peptide or a protein.

Specific examples of the peptide that bind to FcRn in a pH dependent manner include 8D-01 to 8D-06 and 2G01D (SEQ ID NO: 13 to 19, respectively)

[Chemical formula 3]

8D-01

S

[$^{Ac}$D-Nty]F[Nty]LYN[Nna]GDPL[Nty]LCGSGSGS 8D-02

S

[$^{Ac}$D-Nty]QSV[Nty]PDHWS[Pal]CGSGSGS 8D-03

S

[$^{Ac}$D-Nty]F[Nty]W[Nty]IWPKNYCGSGSGS 8D-04

S

[$^{Ac}$D-Nty]VS[Nty]T[Pal][Nty]WYWDCGSGSGS 8D-05

S

[$^{Ac}$D-Nty][Pal]NFGPLWSKLS[Nna]CGSGSGS 8D-06

S

[$^{Ac}$D-Nty]LKS[Nty]LSWVYKSCGSGSGS

[Chemical formula 4]

2G01D

S

[$^{Ac}$D-Nty]F[Nty]LYN[Nna]GDPL[Nty]LCG-$ONH_2$

The peptide 2G01D is a cyclic peptide composed of 15 amino acids including four special amino acids undergoing a pH-dependent change in the charge of a side chain thereof.

As will be shown later in Examples, a dissociation constant for binding between this cyclic peptide and FcRn was different by nearly 70 times between that at pH 7.4 and that at pH 6.0.

The present invention also provides a kit with which the screening method of the present invention is carried out. No particular limitation is imposed on the details of the kit, but it may be equipped with various reagents including a pH regulator and special amino acid that undergoes a pH-dependent change in the charge of the side chain thereof, various libraries, a buffer, and the like. It may be equipped further with a necessary tool, an instruction manual, and the like.

Disclosure of all the patent documents and non-patent documents cited herein is incorporated herein by reference in its entirety.

Examples

The present invention will hereinafter be described specifically based on examples but the present invention is not limited to or by them. Those skilled in the art can change the present invention into various embodiments without departing from the spirit of the present invention and such a change is also embraced within the scope of the present invention.

[Preparation of NNK mRNA Library]

First, a double-stranded DNA having the following sequence was prepared (only the Forward chain will hereinafter be described in order of 5'→3'):

(SEQ ID NO: 20)
TAATACGACTCACTATAGGGTTAACTTTAAGAAGGAGATATACAT(ATG)

(NNK)₁(NNK)₂ . . .

(NNK)n(TGC)(GGC)(AGC)(GGC)(AGC)(GGC)(AGC)(TAG)

GACGGGGGGCGGAAA (wherein a single codon in the ORF region is indicated in ( ), N represents any one of A, T, G, and C, K represents either one of T and G, and n stands for nine numbers from 4 to 12).

Then, the DNA was transcribed using T7 RNA polymerase to obtain an mRNA having the following sequence:

(SEQ ID NO: 21)
GGGUUAACUUUAAGAAGGAGAUAUACAU(AUG)(NNK)₁(NNK)₂ . . .

(NNK)ₙ(UGC)(GGC)(AGC)(GGC)(AGC)(GGC)(AGC)(UAG)

GACGGGGGGCGGAAA (wherein, N represents any one of A, U, G, and C and K represents either one of U and G).

[RNA Display]

By repeating the following cycle from "liking to a puromycin linker" to "amplification of sequence information of the peptide recovered", peptides that bind to FcRn were selected from a random peptide library. A conceptual diagram of RNA display is shown in FIG. 1.

[1] Linking to Puromycin Linker

A puromycin linker represented by the following sequence was annealed with the above-mentioned mRNA library and they were linked via T4 RNA ligase (SPC18 represents PEG in which the total number of C and O is 18; and Pu represents puromycin).

(SEQ ID NO: 22)
pdCTCCCGCCCCCCGTCC(SPC18)₅CC(Pu)

[2] Translation

Figure 2:
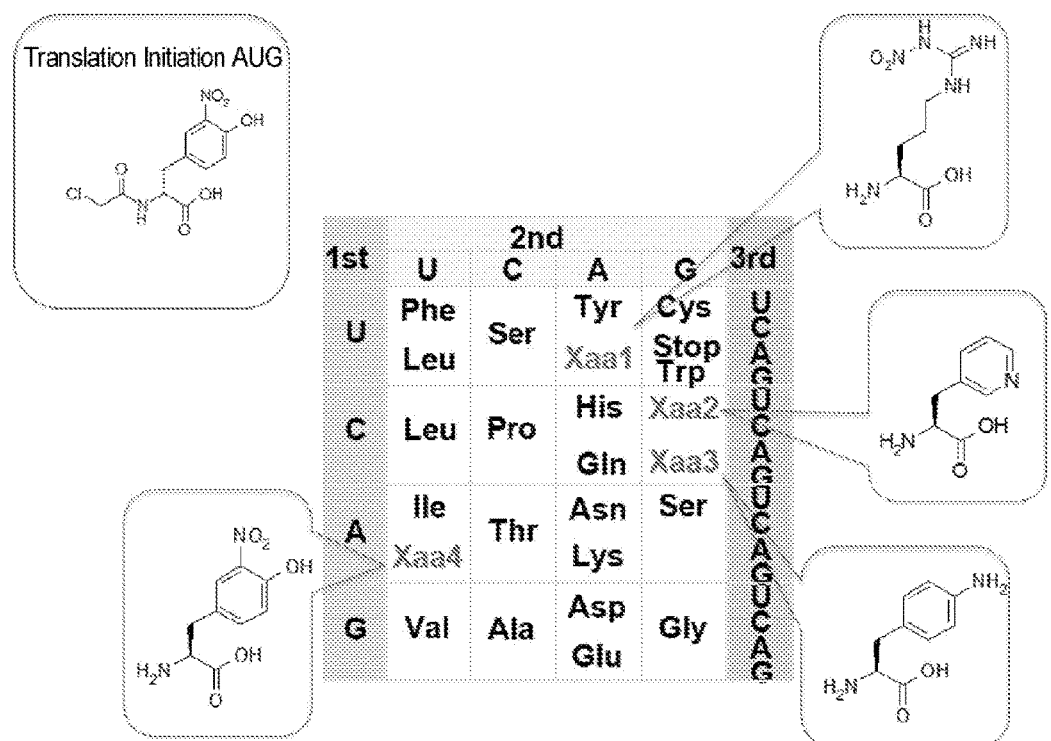
FIG. 2 is an modified genetic code table used in Examples.

The mRNA linked to the linker was translated using a modified genetic code table shown in FIG. 2. In the present Example, translation was performed using a translation system constructed by removing methionine and arginine from typical 20 amino acids and instead, adding five tRNAs prepared using flexizyme, that is, (i) tRNA$^{fMet}_{CAU}$ to which α-N-chloroacetyl-3-nitro-D-tyrosine (ClAc-D-Nty) has been linked, (ii) tRNA$^{AsnE2}_{CAU}$ to which 3-nitro-L-tyrosine (Nty) has been linked, (iii) tRNA$^{AsnE2}_{CUA}$ to which ω-N-nitro-L-arginine (Nna) has been linked, (iv) tRNA$^{AsnE2}_{ACG}$ to which 3-pyridyl-L-alanine (PaI) has been linked, and (v) tRNA$^{AsnE2}_{CCG}$ to which 4-amino-L-phenylalanine (Aph) has been linked.

As a result of the translation, a peptide library containing, in the random sequence thereof, non-protein amino acids (i) to (v) and cyclized through a thioether bond is synthesized and the mRNA and the peptide are linked to each other due to binding of Pu to the C terminal of the peptide.

[3] Acquisition of Peptide that Binds to FcRn

The special cyclic peptide library thus prepared was mixed with human soluble FcRn chemically biotinated with NHS-biotin and the resulting mixture was stirred at 4° C. for 30 minutes in an MES buffer of pH 6.0. Streptavidin magnetic beads were added further and the resulting mixture was stirred at 4° C. for 5 minutes. The supernatant was removed using a magnet and remaining magnetic particles were washed with an MES buffer of pH 6.0.

A PCR solution was added to the beads and the resulting mixture was heated at 95° C. for 5 minutes. The peptide was released from the beads and the supernatant was recovered.

[4] Amplification of Sequence Information of Peptide Recovered

The peptide-mRNA recovered while being bound to FcRn was reverse transcribed into the cDNA, followed by amplification by PCR. The DNA thus obtained was transcribed into the mRNA. After Round 2, reverse transcription was performed immediately after linking between the mRNA and the peptide in order to prevent selection of an RNA aptamer.

[5] Identification of Peptide Sequence Selected

The above-mentioned series of operations was repeated to concentrate the sequence that specifically binds to FcRn.

[Results of Selection]

Figure 3:
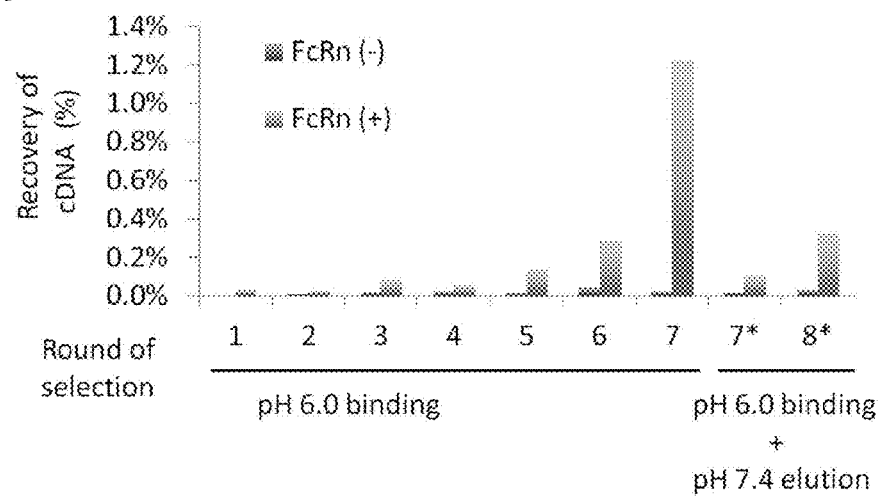
FIG. 3 shows screening results of FcRn-binding peptides by mRNA display.

Results of selection are shown in FIG. 3.

As a result of acquisition of the FcRn-bound peptide by mRNA display, an FcRn-dependent increase in a recovery rate of cDNA was confirmed in Round 6. After Round 6 was therefore performed again, an MES buffer of pH 7.4 was added to beads washed with an MES buffer of pH 6.0, and the resulting mixture was stirred at room temperature for 20 minutes, the supernatant was recovered. Continuously, in Round 7, elution was performed similarly. As a result, an increase in recovery rate of cDNA was confirmed again.

[Identification of Peptide Sequence Selected]

After Round 7, TA cloning was performed using the DNA amplified by PCR and the peptide sequence thus obtained was identified. The results are shown in the following table.

[Chemical formula 5]

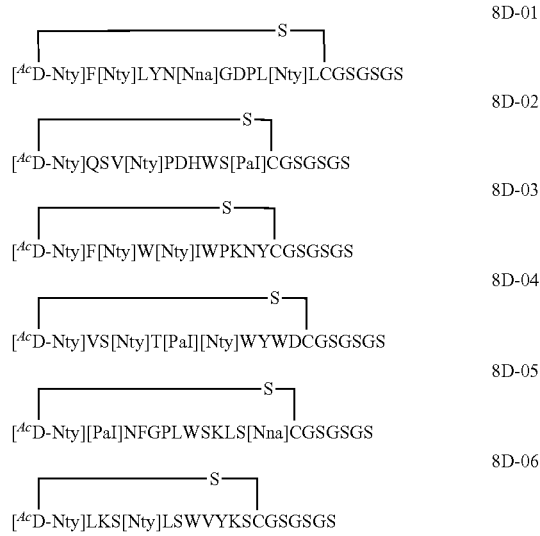

[Evaluation of pH Dependent Binding of the Selected Peptide to FcRn]

The peptide 8D-01 that had exhibited the highest appearance frequency among the selected peptide sequences was cloned and used to evaluate for binding ability by using the above-mentioned mRNA display. Upon interaction between FcRn and the peptide-mRNA, an MES buffer of pH 6.0 or pH 7.4 was used. Elution of the peptide-mRNA was performed by adding a PCR solution to beads and heating the resulting mixture at 95° C. for 5 minutes. Then, the peptide was released from the beads and the supernatant was recovered.

Figure 4:
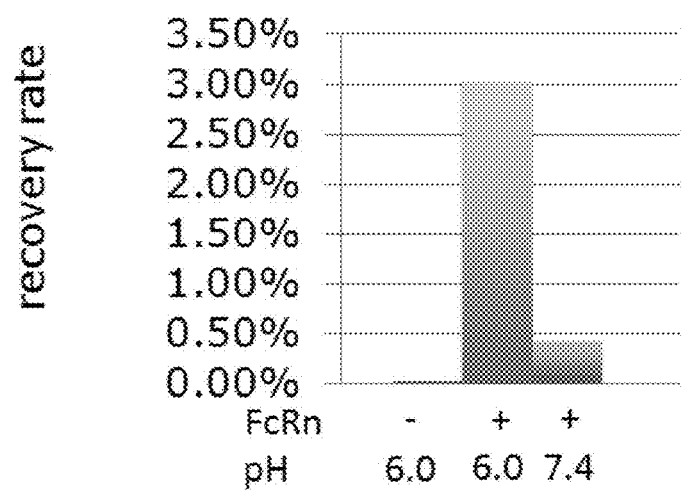
FIG. 4 shows evaluation results of the binding ability, at pH 6.0 and pH 7.4, of a 8D-01 clone found to show the highest appearance frequency based on the screening results shown in FIG. 3.
Figure 5A:
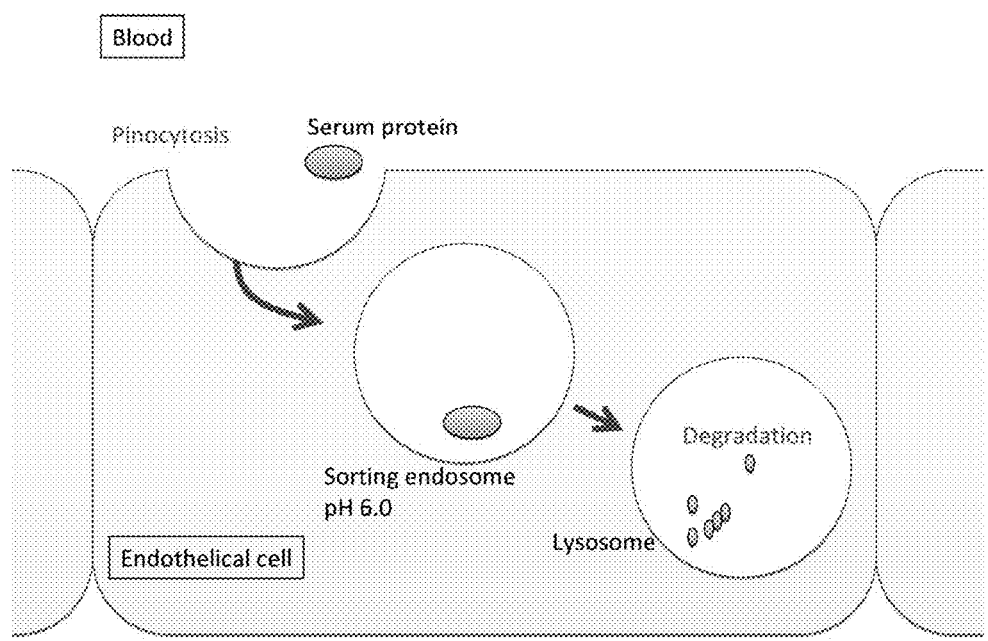
FIG. 5A is a conceptual diagram showing that a protein or peptide in the blood is brought in an endosome by pinocytosis and degraded in a lysosome.
Figure 5B:
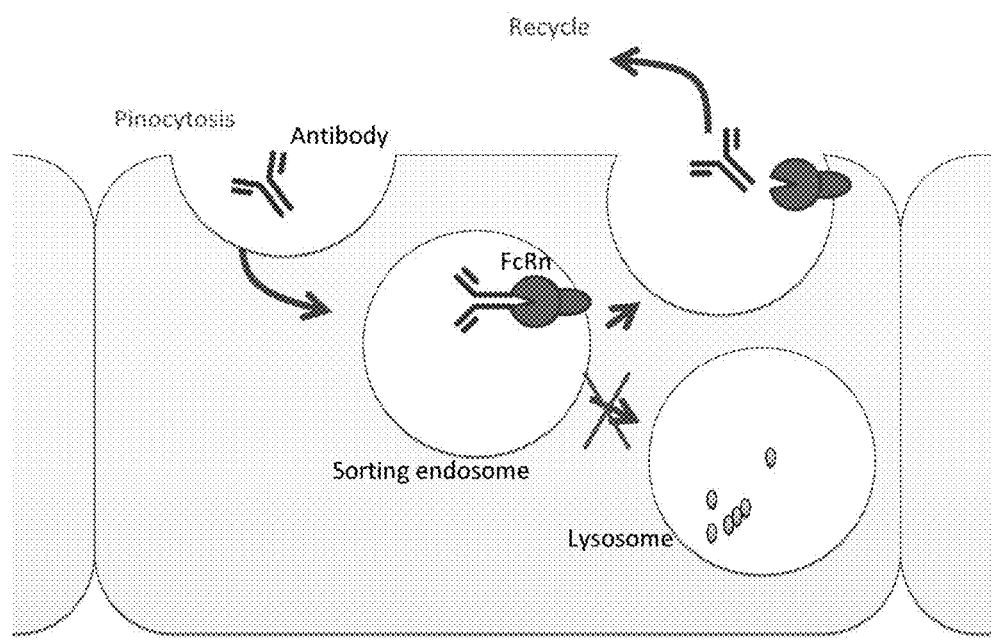
FIG. 5B is a conceptual diagram showing that an antibody binds to FcRn in an endosome, is presented extracellularly again through a pathway of exocytosis, and returns to the blood.

The results are shown in FIG. 4. When the peptide and FcRn were reacted with each other while using the buffer of pH 6.0, a recovery rate of cDNA was remarkably higher than that when the buffer of pH 7.4 was used, showing a change in the recovery rate of cDNA, depending on the pH of the buffer.

[Evaluation on pH Dependent Binding of a Solid-Phase Synthesized Peptide to FcRn]

In order to find whether a peptide alone interacts with FcRn in a pH dependent manner, the peptide 2G01D not having SGSGS on the C-terminal side of 8D-01 and amidated at the C-terminal was synthesized on a solid phase and a dissociation constant Kd binding constant was measured using Biacore T100 (GE Healthcare). FcRn was immobilized onto a sensor chip by an amine coupling method. The following is the peptide 2G01D:

[Chemical formula 6]

[$^{Ac}$D-Nty]F[Nty]LYN[Nna]GDPL[Nty]LCG-ONH$_2$

2G01D

On the other hand, a solid-phase synthesized peptide 2G01D was added as an analyte to a phosphate buffer having a pH 6.0 or 7.4 and a dissociation constant was measured.

The results are shown in the following table. The dissociation constant was 4.3 nM at pH 6.0 and 290 nM at pH 7.4, showing a pH-dependent change in dissociation constant by about 70 times.

TABLE 2

|  | $k_{on}$(1/Ms) | $k_{off}$(1/s) | $K_D$ (M) |
| --- | --- | --- | --- |
| pH 7.4 | $3.26 \times 10^4$ | $9.55 \times 10^{-3}$ | $2.93 \times 10^{-7}$ |
| pH 6.0 | $9.25 \times 10^5$ | $3.94 \times 10^{-3}$ | $4.26 \times 10^{-9}$ |

SEQUENCE LISTING

```
<160> NUMBER OF SEQ ID NOS: 22

<210> SEQ ID NO 1
<211> LENGTH: 12
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (2)..(2)
<223> OTHER INFORMATION: Xaa stands for 3-nitro-L-tyrosine.
<220> FEATURE:
<221> NAME/KEY: MISC_FEATURE
<222> LOCATION: (6)..(6)
<223> OTHER INFORMATION: Xaa stands for N omega-nitro-L-arginine.
<220> FEATURE:
<221> NAME/KEY: MISC_FEATURE
<222> LOCATION: (11)..(11)
<223> OTHER INFORMATION: Xaa stands for 3-nitro-L-tyrosine.

<400> SEQUENCE: 1

Phe Xaa Leu Tyr Asn Xaa Gly Asp Pro Leu Xaa Leu
1               5                   10

<210> SEQ ID NO 2
<211> LENGTH: 10
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (4)..(4)
<223> OTHER INFORMATION: Xaa stands for 3-nitro-L-tyrosine.
<220> FEATURE:
<221> NAME/KEY: MISC_FEATURE
<222> LOCATION: (10)..(10)
<223> OTHER INFORMATION: Xaa stands for 3-pyridyl-L-Alanine

<400> SEQUENCE: 2

Gln Ser Val Xaa Pro Asp His Trp Ser Xaa
1               5                   10
```

```
<210> SEQ ID NO 3
<211> LENGTH: 10
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (2)..(2)
<223> OTHER INFORMATION: Xaa stands for 3-nitro-L-tyrosine.
<220> FEATURE:
<221> NAME/KEY: MISC_FEATURE
<222> LOCATION: (4)..(4)
<223> OTHER INFORMATION: Xaa stands for 3-nitro-L-tyrosine.

<400> SEQUENCE: 3

Phe Xaa Trp Xaa Ile Trp Pro Lys Asn Tyr
1               5                   10

<210> SEQ ID NO 4
<211> LENGTH: 10
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (3)..(3)
<223> OTHER INFORMATION: Xaa stands for 3-nitro-L-tyrosine.
<220> FEATURE:
<221> NAME/KEY: MISC_FEATURE
<222> LOCATION: (5)..(5)
<223> OTHER INFORMATION: Xaa stands for 3-pyridyl-L-alanine.
<220> FEATURE:
<221> NAME/KEY: MISC_FEATURE
<222> LOCATION: (6)..(6)
<223> OTHER INFORMATION: Xaa stands for 3-nitro-L-tyrosine.

<400> SEQUENCE: 4

Val Ser Xaa Thr Xaa Xaa Trp Tyr Trp Asp
1               5                   10

<210> SEQ ID NO 5
<211> LENGTH: 12
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for 3-pyridyl-L-alanine
<220> FEATURE:
<221> NAME/KEY: MISC_FEATURE
<222> LOCATION: (12)..(12)
<223> OTHER INFORMATION: Xaa stands for N-omega-nitro-L-arginine.

<400> SEQUENCE: 5

Xaa Asn Phe Gly Pro Leu Trp Ser Lys Leu Ser Xaa
1               5                   10

<210> SEQ ID NO 6
<211> LENGTH: 11
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
```

```
<222> LOCATION: (4)..(4)
<223> OTHER INFORMATION: Xaa stands for 3-nitro-L-tyrosine.

<400> SEQUENCE: 6

Leu Lys Ser Xaa Leu Ser Trp Val Tyr Lys Ser
1               5                   10

<210> SEQ ID NO 7
<211> LENGTH: 14
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(14)
<223> OTHER INFORMATION: A thioether bond may be formed.
<220> FEATURE:
<221> NAME/KEY: MISC_FEATURE
<222> LOCATION: (3)..(3)
<223> OTHER INFORMATION: Xaa stands for 3-nitro-L-tyrosine.
<220> FEATURE:
<221> NAME/KEY: MISC_FEATURE
<222> LOCATION: (7)..(7)
<223> OTHER INFORMATION: Xaa stands for N omega-nitro-L-arginine.
<220> FEATURE:
<221> NAME/KEY: MISC_FEATURE
<222> LOCATION: (12)..(12)
<223> OTHER INFORMATION: Xaa stands for 3-nitro-L-tyrosine.

<400> SEQUENCE: 7

Xaa Phe Xaa Leu Tyr Asn Xaa Gly Asp Pro Leu Xaa Leu Cys
1               5                   10

<210> SEQ ID NO 8
<211> LENGTH: 12
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(12)
<223> OTHER INFORMATION: A thioether bond may be formed.
<220> FEATURE:
<221> NAME/KEY: MISC_FEATURE
<222> LOCATION: (5)..(5)
<223> OTHER INFORMATION: Xaa stands for 3-nitro-L-tyrosine.
<220> FEATURE:
<221> NAME/KEY: MISC_FEATURE
<222> LOCATION: (11)..(11)
<223> OTHER INFORMATION: Xaa stands for 3-pyridyl-L-alanine.

<400> SEQUENCE: 8

Xaa Gln Ser Val Xaa Pro Asp His Trp Ser Xaa Cys
1               5                   10

<210> SEQ ID NO 9
<211> LENGTH: 12
<212> TYPE: PRT
<213> ORGANISM: Artificial
<220> FEATURE:
<223> OTHER INFORMATION: A pepide that binds to FcRn in a pH-dependent
```

```
manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(12)
<223> OTHER INFORMATION: A thioether bond may be formed.
<220> FEATURE:
<221> NAME/KEY: MISC_FEATURE
<222> LOCATION: (3)..(3)
<223> OTHER INFORMATION: Xaa stands for 3-nitro-L-tyrosine.
<220> FEATURE:
<221> NAME/KEY: MISC_FEATURE
<222> LOCATION: (5)..(5)
<223> OTHER INFORMATION: Xaa stands for 3-nitro-L-tyrosine.

<400> SEQUENCE: 9

Xaa Phe Xaa Trp Xaa Ile Trp Pro Lys Asn Tyr Cys
1               5                   10

<210> SEQ ID NO 10
<211> LENGTH: 12
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(12)
<223> OTHER INFORMATION: A thioether bond may be formed.
<220> FEATURE:
<221> NAME/KEY: MISC_FEATURE
<222> LOCATION: (4)..(4)
<223> OTHER INFORMATION: Xaa stands for 3-nitro-L-tyrosine.
<220> FEATURE:
<221> NAME/KEY: MISC_FEATURE
<222> LOCATION: (6)..(6)
<223> OTHER INFORMATION: Xaa stands for 3-pyridyl-L-alanine.
<220> FEATURE:
<221> NAME/KEY: MISC_FEATURE
<222> LOCATION: (7)..(7)
<223> OTHER INFORMATION: Xaa stands for 3-nitro-L-tyrosine.

<400> SEQUENCE: 10

Xaa Val Ser Xaa Thr Xaa Xaa Trp Tyr Trp Asp Cys
1               5                   10

<210> SEQ ID NO 11
<211> LENGTH: 14
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(14)
<223> OTHER INFORMATION: A thioether bond may be formed.
<220> FEATURE:
<221> NAME/KEY: MISC_FEATURE
<222> LOCATION: (2)..(2)
<223> OTHER INFORMATION: Xaa stands for 3-pyridyl-L-alanine.
<220> FEATURE:
<221> NAME/KEY: MISC_FEATURE
```

```
<222> LOCATION: (13)..(13)
<223> OTHER INFORMATION: Xaa stands for N omega-nitro-L-arginine.

<400> SEQUENCE: 11

Xaa Xaa Asn Phe Gly Pro Leu Trp Ser Lys Leu Ser Xaa Cys
1               5                   10

<210> SEQ ID NO 12
<211> LENGTH: 13
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(13)
<223> OTHER INFORMATION: A thioether bond may be formed.
<220> FEATURE:
<221> NAME/KEY: MISC_FEATURE
<222> LOCATION: (5)..(5)
<223> OTHER INFORMATION: Xaa stands for 3-nitro-L-tyrosine.

<400> SEQUENCE: 12

Xaa Leu Lys Ser Xaa Leu Ser Trp Val Tyr Lys Ser Cys
1               5                   10

<210> SEQ ID NO 13
<211> LENGTH: 20
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(14)
<223> OTHER INFORMATION: A thioether bond may be formed.
<220> FEATURE:
<221> NAME/KEY: MISC_FEATURE
<222> LOCATION: (3)..(3)
<223> OTHER INFORMATION: Xaa stands for 3-nitro-L-tyrosine.
<220> FEATURE:
<221> NAME/KEY: MISC_FEATURE
<222> LOCATION: (7)..(7)
<223> OTHER INFORMATION: Xaa stands for N omega-nitro-L-arginine.
<220> FEATURE:
<221> NAME/KEY: MISC_FEATURE
<222> LOCATION: (12)..(12)
<223> OTHER INFORMATION: Xaa stands for 3-nitro-L-tyrosine.

<400> SEQUENCE: 13

Xaa Phe Xaa Leu Tyr Asn Xaa Gly Asp Pro Leu Xaa Leu Cys Gly Ser
1               5                   10                  15

Gly Ser Gly Ser
            20

<210> SEQ ID NO 14
<211> LENGTH: 18
<212> TYPE: PRT
<213> ORGANISM: Artificial
<220> FEATURE:
<223> OTHER INFORMATION: A pepide that binds to FcRn in a pH-dependent
      manner.
```

```
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(12)
<223> OTHER INFORMATION: A thioether bond may be formed.
<220> FEATURE:
<221> NAME/KEY: MISC_FEATURE
<222> LOCATION: (5)..(5)
<223> OTHER INFORMATION: Xaa stands for 3-nitro-L-tyrosine.
<220> FEATURE:
<221> NAME/KEY: MISC_FEATURE
<222> LOCATION: (11)..(11)
<223> OTHER INFORMATION: Xaa stands for 3-pyridyl-L-alanine.

<400> SEQUENCE: 14

Xaa Gln Ser Val Xaa Pro Asp His Trp Ser Xaa Cys Gly Ser Gly Ser
1               5                   10                  15

Gly Ser

<210> SEQ ID NO 15
<211> LENGTH: 18
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(12)
<223> OTHER INFORMATION: A thioether bond may be formed.
<220> FEATURE:
<221> NAME/KEY: MISC_FEATURE
<222> LOCATION: (3)..(3)
<223> OTHER INFORMATION: Xaa stands for 3-nitro-L-tyrosine.
<220> FEATURE:
<221> NAME/KEY: MISC_FEATURE
<222> LOCATION: (5)..(5)
<223> OTHER INFORMATION: Xaa stands for 3-nitro-L-tyrosine.

<400> SEQUENCE: 15

Xaa Phe Xaa Trp Xaa Ile Trp Pro Lys Asn Tyr Cys Gly Ser Gly Ser
1               5                   10                  15

Gly Ser

<210> SEQ ID NO 16
<211> LENGTH: 18
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(12)
<223> OTHER INFORMATION: A thioether bond may be formed.
<220> FEATURE:
<221> NAME/KEY: MISC_FEATURE
<222> LOCATION: (4)..(4)
<223> OTHER INFORMATION: Xaa stands for 3-nitro-L-tyrosine.
<220> FEATURE:
<221> NAME/KEY: MISC_FEATURE
<222> LOCATION: (6)..(6)
```

```
<223> OTHER INFORMATION: Xaa stands for 3-pyridyl-L-alanine.
<220> FEATURE:
<221> NAME/KEY: MISC_FEATURE
<222> LOCATION: (7)..(7)
<223> OTHER INFORMATION: Xaa stands for 3-nitro-L-tyrosine.

<400> SEQUENCE: 16

Xaa Val Ser Xaa Thr Xaa Xaa Trp Tyr Trp Asp Cys Gly Ser Gly Ser
1               5                   10                  15

Gly Ser

<210> SEQ ID NO 17
<211> LENGTH: 20
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(14)
<223> OTHER INFORMATION: A thioether bond may be formed.
<220> FEATURE:
<221> NAME/KEY: MISC_FEATURE
<222> LOCATION: (2)..(2)
<223> OTHER INFORMATION: Xaa stands for 3-pyridyl-L-alanine.
<220> FEATURE:
<221> NAME/KEY: MISC_FEATURE
<222> LOCATION: (13)..(13)
<223> OTHER INFORMATION: Xaa stands for N omega-nitro-L-arginine.

<400> SEQUENCE: 17

Xaa Xaa Asn Phe Gly Pro Leu Trp Ser Lys Leu Ser Xaa Cys Gly Ser
1               5                   10                  15

Gly Ser Gly Ser
            20

<210> SEQ ID NO 18
<211> LENGTH: 19
<212> TYPE: PRT
<213> ORGANISM: Artificial
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(13)
<223> OTHER INFORMATION: A thioether bond may be formed.
<220> FEATURE:
<221> NAME/KEY: MISC_FEATURE
<222> LOCATION: (5)..(5)
<223> OTHER INFORMATION: Xaa stands for 3-nitro-L-tyrosine.

<400> SEQUENCE: 18

Xaa Leu Lys Ser Xaa Leu Ser Trp Val Tyr Lys Ser Cys Gly Ser Gly
1               5                   10                  15

Ser Gly Ser

<210> SEQ ID NO 19
<211> LENGTH: 15
<212> TYPE: PRT
<213> ORGANISM: Artificial
```

```
<220> FEATURE:
<223> OTHER INFORMATION: A pepide that binds to FcRn in a pH-dependent
      manner.
<220> FEATURE:
<221> NAME/KEY: MISC_FEATURE
<222> LOCATION: (1)..(1)
<223> OTHER INFORMATION: Xaa stands for N-acetyl-3-nitro-D-tyrosine.
<220> FEATURE:
<221> NAME/KEY: MISC_FEATURE
<222> LOCATION: (1)..(14)
<223> OTHER INFORMATION: A thioether bond may be formed.
<220> FEATURE:
<221> NAME/KEY: MISC_FEATURE
<222> LOCATION: (3)..(3)
<223> OTHER INFORMATION: Xaa stands for 3-nitro-L-tyrosine.
<220> FEATURE:
<221> NAME/KEY: MISC_FEATURE
<222> LOCATION: (7)..(7)
<223> OTHER INFORMATION: Xaa stands for N omega-nitro-L-arginine.
<220> FEATURE:
<221> NAME/KEY: MISC_FEATURE
<222> LOCATION: (12)..(12)
<223> OTHER INFORMATION: Xaa stands for 3-nitro-L-tyrosine.
<220> FEATURE:
<221> NAME/KEY: MOD_RES
<222> LOCATION: (15)..(15)
<223> OTHER INFORMATION: AMIDATION

<400> SEQUENCE: 19

Xaa Phe Xaa Leu Tyr Asn Xaa Gly Asp Pro Leu Xaa Leu Cys Gly
1               5                   10                  15

<210> SEQ ID NO 20
<211> LENGTH: 90
<212> TYPE: DNA
<213> ORGANISM: Artificial
<220> FEATURE:
<223> OTHER INFORMATION: DNA sequence encoding NNK mRNA library.
<220> FEATURE:
<221> NAME/KEY: misc_feature
<222> LOCATION: (49)..(49)
<223> OTHER INFORMATION: N stands for any base.
<220> FEATURE:
<221> NAME/KEY: misc_feature
<222> LOCATION: (50)..(50)
<223> OTHER INFORMATION: N stands for any base.
<220> FEATURE:
<221> NAME/KEY: misc_feature
<222> LOCATION: (51)..(51)
<223> OTHER INFORMATION: N stands for T or G.
<220> FEATURE:
<221> NAME/KEY: misc_feature
<222> LOCATION: (49)..(51)
<223> OTHER INFORMATION: This sequence may be repeated 4 to 12 times.

<400> SEQUENCE: 20
taatacgact cactataggg ttaacttaa gaaggagata tacatatgnn ntgcggcagc    60
ggcagcggca gctaggacgg ggggcggaaa                                   90

<210> SEQ ID NO 21
<211> LENGTH: 73
<212> TYPE: RNA
<213> ORGANISM: Artificial
<220> FEATURE:
<223> OTHER INFORMATION: RNA sequence of NNK mRNA library.
<220> FEATURE:
<221> NAME/KEY: misc_feature
<222> LOCATION: (32)..(32)
<223> OTHER INFORMATION: N stands for any base.
<220> FEATURE:
<221> NAME/KEY: misc_feature
<222> LOCATION: (33)..(33)
<223> OTHER INFORMATION: N stands for any base.
<220> FEATURE:
```

-continued

```
<221> NAME/KEY: misc_feature
<222> LOCATION: (34)..(34)
<223> OTHER INFORMATION: N stands for U or G.
<220> FEATURE:
<221> NAME/KEY: misc_feature
<222> LOCATION: (32)..(34)
<223> OTHER INFORMATION: This sequence may be repeated 4 to 12 times.

<400> SEQUENCE: 21
ggguuaacuu uaagaaggag auauacauau gnnnugcggc agcggcagcg gcagcuagga      60 cgggggggcgg aaa                                                        73

<210> SEQ ID NO 22
<211> LENGTH: 16
<212> TYPE: DNA
<213> ORGANISM: Artificial
<220> FEATURE:
<223> OTHER INFORMATION: Puromycin linker.
<220> FEATURE:
<221> NAME/KEY: modified_base
<222> LOCATION: (1)..(1)
<223> OTHER INFORMATION: PHOSPHORYLATION
<220> FEATURE:
<221> NAME/KEY: misc_feature
<222> LOCATION: (16)..(16)
<223> OTHER INFORMATION: Cytosine residue to which (SPC18)5CC(Pu) is
      linked. SPC18 stands for PEG in which the total number of C and O
      is 18.

<400> SEQUENCE: 22
ctcccgcccc ccgtcc                                                      16
```

The invention claimed is:

1. A screening method for selecting peptides that consist of 3 to 50 amino acids and bind to a target molecule at a first pH and do not bind to the target molecule at a second pH, comprising:

synthesizing a nucleic acid library in which nucleic acids respectively encode peptides containing at least one special amino acid that undergoes a pH-dependent change in the charge of the side chain thereof;

using the nucleic acid library to express the peptides and prepare a peptide library;

bringing the peptide library into contact with the target molecule and incubating them under the first pH condition and selecting peptides that bind to the target molecule; and selecting, from the peptides that have bound to the target molecule, peptides that do not bind to the target molecule under the second pH condition.

2. A screening method for selecting peptides that consist of 3 to 50 amino acids and bind to a target molecule at a first pH and do not bind to the target molecule at a second pH, comprising:

synthesizing a peptide-nucleic acid complex library in which peptides containing at least one special amino acid that undergoes a pH-dependent change in the charge of the side chain thereof have bound to nucleic acids encoding the peptides;

(a) bringing the peptide-nucleic acid complex library into contact with the target molecule and incubating them under the first pH condition and selecting peptide-nucleic acid complexes that bind to the target molecule;

(b) obtaining a nucleic acid library including nucleic acids of the selected peptide-nucleic acid complexes and preparing therefrom a peptide-nucleic acid complex library;

carrying out the step (a) and the step (b) once or more;

carrying out the step (a) again, eluting the peptide-nucleic acid complexes that have bound to the target molecule under the second pH condition, and identifying the peptides thus eluted.

3. The method according to claim 1, wherein the amino acid that undergoes a pH-dependent change in the charge of the side chain thereof contains, in the side chain, a functional group that undergoes a change in protonated state at pH from 6 to 8.

4. The method according to claim 1, wherein the amino acid that undergoes a pH-dependent change in the charge of the side chain thereof is selected from the followings:

tyrosine having at the 3-position or at the 3- and 5-positions thereof, $NO_2$, Cl, Br, I, $SO_2R$ (R representing OH, $NH_2$, or Ar), COR (R representing OH, $NH_2$, Ar, $CF_3$, or $C_6F_5$), CN, $CF_3$, or $C_6F$, or N-substituted derivatives thereof;

arginine having at the Nω-position thereof, $NO_2$, $SO_2R$ (R representing OH, $NH_2$, or Ar), COR (R representing OH, $NH_2$, Ar, $CF_3$, or $C_6F_5$), CN, $CF_3$, or $C_6F_5$, or N-substituted derivatives thereof;

phenylalanine having at the 2-, 3-, or 4-position thereof an amino group, or N-substituted derivatives thereof; and 2-pyridylalanine, 3-pyridylalanine, or 4-pyridylalanine, or N-substituted derivatives thereof.

5. The method according to claim 1, wherein the amino acid that undergoes a pH-dependent change in the charge of the side chain thereof is selected from the following group:

Chemical formula 1

[Structural formulas of four amino acid derivatives shown]

6. The method according to claim 1, wherein the peptides are each a cyclic peptide.

7. A screening method for selecting peptides binding specifically to a protein expressed in cancer cells,
wherein in the method as claimed in claim 1, the protein expressed in cancer cells is used as the target molecule, the first pH is made weakly acidic, and the second pH is made weakly basic.

8. A screening method for selecting peptides to be recycled after pinocytosis, wherein in the method as claimed in claim 1, a neonatal Fc receptor (FcRn) is used as the target molecule, the first pH is made weakly acidic, and the second pH is made weakly basic.

9. The method according to claim 1, wherein the target molecule is an antigen or a cytokine receptor.

10. A FcRn-binding peptide comprising any one of the following amino acid sequences or an amino acid sequence having one or several amino acid additions, substitutions, or deletions in the following amino acid sequences and containing at least one amino acid selected from the group consisting of Nty, Nna, and Pal;

F[Nty]LYN[Nna]GDPL[Nty]L, (SEQ ID NO: 1)

QSV[Nty]PDHWS[Pal], (SEQ ID NO: 2)

F[Nty]W[Nty]IWPKNY, (SEQ ID NO: 3)

VS[Nty]T[Pal][Nty]WYWD, (SEQ ID NO: 4)

[Pal]NFGPLWSKLS[Nna], (SEQ ID NO: 5)
and

LKS[Nty]LSWVYKS (SEQ ID NO: 6)

wherein, Nty represents 3-nitro-L-tyrosine, Nna represents Nω-nitro-L-arginine, and Pal represents 3-pyridyl-L-alanine.

11. A FcRn-binding peptide comprising any one of the following amino acid sequences or an amino acid sequence having one or several amino acid additions, substitutions, or deletions in the following amino acid sequences and containing at least one amino acid selected from the group consisting of $^{Ac}$D-Nty, Nty, Nna, and Pal;

[$^{Ac}$D-Nty]F[Nty]LYN[Nna]GDPL[Nty]LC, (SEQ ID NO: 7)

[$^{Ac}$D-Nty]QSV[Nty]PDHWS[Pal]C, (SEQ ID NO: 8)

[$^{Ac}$D-Nty]F[Nty]W[Nty]IWPKNYC, (SEQ ID NO: 9)

[$^{Ac}$D-Nty]VS[Nty]T[Pal][Nty]WYWDC, (SEQ ID NO: 10)

[$^{Ac}$D-Nty][Pal]NFGPLWSKLS[Nna]C, (SEQ ID NO: 11)
and

[$^{Ac}$D-Nty]LKS[Nty]LSWVYKSC (SEQ ID NO: 12)

wherein, $^{Ac}$D-Nty represents N-acetyl-3-nitro-D-tyrosine, Nty represents 3-nitro-L-tyrosine, Nna represents Nω-nitro-L-arginine, Pal represents 3-pyridyl-L-alanine and each of the peptides may be circularized by a thioether bond between the acetyl group of $^{Ac}$D-Nty and the cysteine residue.

12. A complex of a peptide selected by the method as claimed in claim 1 and a drug.

13. The method according to claim 2, wherein the amino acid that undergoes a pH-dependent change in the charge of the side chain thereof contains, in the side chain, a functional group that undergoes a change in protonated state at pH from 6 to 8.

14. The method according to claim 2, wherein the amino acid that undergoes a pH-dependent change in the charge of the side chain thereof is selected from the followings:
tyrosine having at the 3-position or at the 3- and 5-positions thereof, $NO_2$, Cl, Br, I, $SO_2R$ (R representing OH, $NH_2$, or Ar), COR (R representing OH, $NH_2$, Ar, $CF_3$, or $C_6F_5$), CN, $CF_3$, or $C_6F$, or N-substituted derivatives thereof;
arginine having at the Nω-position thereof, $NO_2$, $SO_2R$ (R representing OH, $NH_2$, or Ar), COR (R representing OH, $NH_2$, Ar, $CF_3$, or $C_6F_5$), CN, $CF_3$, or $C_6F_5$, or N-substituted derivatives thereof;
phenylalanine having at the 2-, 3-, or 4-position thereof an amino group, or N-substituted derivatives thereof; and
2- pyridylalanine, 3-pyridylalanine, or 4-pyridylalanine, or N-substituted derivatives thereof.

15. The method according to claim 2, wherein the amino acid that undergoes a pH-dependent change in the charge of the side chain thereof is selected from the following group:

Chemical formula 1

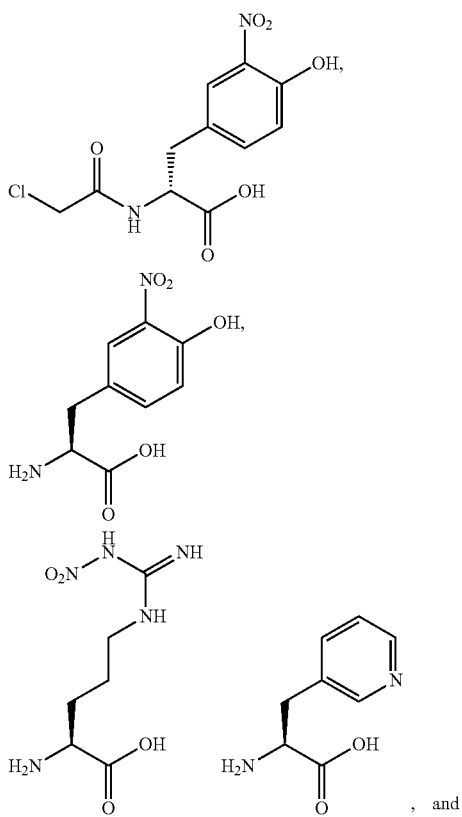
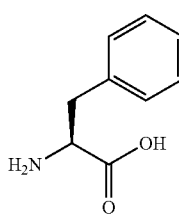
, and

16. The method according to claim 2, wherein the peptides are each a cyclic peptide.

17. A screening method for selecting peptides binding specifically to a protein expressed in cancer cells, wherein in the method as claimed in claim 2, the protein expressed in cancer cells is used as the target molecule, the first pH is made weakly acidic, and the second pH is made weakly basic.

18. A screening method for selecting peptides to be recycled after pinocytosis, wherein in the method as claimed in claim 2, a neonatal Fc receptor (FcRn) is used as the target molecule, the first pH is made weakly acidic, and the second pH is made weakly basic.

19. The method according to claim 2, wherein the target molecule is an antigen or a cytokine receptor.

20. A complex of a peptide selected by the method as claimed in claim 2 and a drug.

21. A complex of a peptide as claimed in claim 10 and a drug.

22. A complex of a peptide as claimed in claim 11 and a drug.

23. The screening method according to claim 1, wherein the peptides consist of 5 to 30 amino acids.

* * * * *